United States Patent [19]

Duffett

[11] Patent Number: Plant 5,915

[45] Date of Patent: Mar. 24, 1987

[54] CHRYSANTHEMUM PLANT NAMED GALLANT

[75] Inventor: William E. Duffett, Salinas, Calif.

[73] Assignee: Yoder Brothers, Inc., Barberton, Ohio

[21] Appl. No.: 644,446

[22] Filed: Aug. 27, 1984

[51] Int. Cl.[4] ..... A01H 5/00

[52] U.S. Cl. ..... Plt./80

[58] Field of Search ..... Plt./76, 80

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Gallant characterized as to uniqueness by the combined characteristics of flat capitulum form, decorative capitulum type, purple ray floret color, diameter across face of capitulum ranging from 10 to 12 cm. at maturity, uniform nine week flowering response, tall plant height when grown single stem, 13 to 20 cm. peduncles on open, normally terminal sprays, 13° C. minimum temperature tolerance for initiation and development of flowering buds, and very high bud count, with six to nine uniformly developed flowers per stem.

3 Drawing Figures

The present invention comprises a new and distinct cultivar of *Chrysanthemum morifolium*, Ramat., named Gallant.

Gallant is a product of a planned breeding program which had the objective of creating new chrysanthemum cultivars having low temperature tolerance for cut spray mum programs with decorative capitulum type, purple ray floret color, eight to nine week flowering response, and the ability to produce commercially acceptable quality in year round programs. Such traits in combination were not present or needed improvement in previously available commercial cultivars. The program was specifically planned to produce a cultivar having similar color and capitulum type to that of Deep Telstar, disclosed in U.S. Plant Pat. No. 3,373, but having one to two weeks shorter response time.

Gallant, identified as 91751022, was originated from a cross made by William E. Duffett in a controlled breeding program in Salinas, Calif. in 1980. The female parent was the cultivar identified as Pink Gin, a commercially available purple decorative whose parentage is unknown to the present inventor. The male parent of Gallant was identified as 79462001, a pink decorative unnamed seedling.

Gallant was discovered and selected as one flowering plant within the progeny of the stated cross by William E. Duffett on Nov. 6, 1981 in a controlled environment in Bogota, Colombia.

The first act of asexual reproduction of Gallant was accomplished when vegetative cuttings were taken from the initial selection in January 1982 in a controlled environment in Bogota, Colombia by a technician working under formulations established and supervised by William E. Duffett through Fernando Jaramillo.

Horticultural examination of selected units initiated Sept. 21, 1982 has demonstrated that the combination of characteristics as herein disclosed for Gallant are firmly fixed and are retained through successive generations of asexual reproduction.

Gallant has not been observed under all possible environmental conditions. The phenotype may vary significantly with variations in environment such as temperature, light intensity, and day length. The following observations, measurements and comparisons describe plants grown in Bogota, Colombia under greenhouse conditions which approximate those generally used in their commercial practice.

The following traits have been repeatedly observed and are determined to be basic characteristics of Gallant which in combination distinguish this Chrysanthemum as a new and distinct cultivar:

(1) Flat capitulum form.

(2) Decorative capitulum type.

(3) Purple ray floret color.

(4) Diameter across face of capitulum ranging from 10 to 12 cm. at maturity.

(5) Uniform nine week photoperiodic flowering response to short days.

(6) Medium peduncle length, ranging from 13 to 20 cm.

(7) Tall plant height, requiring two long day weeks prior to short days to attain a flowered plant height of 100 to 110 cm. for year around flowerings.

(8) Low temperature tolerance of 13° C. for initiation and development when grown in single stem cut spray programs with a continuous dark period of 12 hours.

(9) Very high bud count, with six to nine uniformly developed flowers per stem.

The accompanying photographic drawings show typical inflorescence and leaf characteristics of Gallant, with the colors being as nearly true as possible with illustrations of this type.

Sheet 1 is a color photograph of Gallant grown as a single stem cut spray.

Sheet 2 is a black and white photograph of three views of the inflorescence of Gallant.

Sheet 3 is a black and white photograph showing the upper and under surfaces of leaves of Gallant at three stages of development (mature, intermediate, and immature).

Of the many commercial cultivars known to the present inventor, the most similar in comparison to Gallant is Deep Telstar, referred to above. Reference is made to attached Chart A which compares certain characteristics of Gallant to those same characteristics of Deep Telstar. Gallant has greater vigor or plant height, at least one week shorter response period and therefore shorter overall crop time. Gallant has similar inflorescence color, type, form, peduncle length, capitulum diameter and tolerance of low temperature for bud initiation and development.

In the following description, color references are made to The Royal Horticultural Society Colour Chart. The color values were determined between 11:00 A.M. and 11:15 A.M. on Jan. 6, 1984 under 380 foot-candle light intensity at Salinas, Calif.

Classification:

*Botanical.*—*Chrysanthemum morifolium,* Ramat., cv Gallant.

*Commercial.*—Decorative cut spray mum.

INFLORESCENCE

A. Capitulum:

*Form.*—Flat.

*Type.*—Decorative.

*Diameter across face.*—10 to 12 cm.

B. Corolla of ray florets:

*Color (general tonality from a distance of three meters).*—Purple.

*Color (upper surface).*—75B, fading to 75C and to 75D at the tip of the petals.

*Color (under surface).*—75D.

*Shape.*—Flat and spooned.

C. Corolla of disc florets:

*Color (mature).*—154D.

*Color (immature).*—154A.

D. Reproductive organs:

*Androecium.*—Present disc florets only; scant pollen.

*Gynoecium.*—Present both ray and disc florets.

PLANT

A. General appearance:

*Height.*—Tall; 100 to 110 cm., as a flowering plant from a rooted cutting, with fourteen long days for year around flowerings with a minimum nightly 12 hour continuous dark period.

B. Foliage:

*Color (upper surface).*—146A.

*Color (under surface).*—147B.

*Shape.*—Deeply lobed and moderately serrated.

CHART A
COMPARISON OF GALLANT AND DEEP TELSTAR

| CULTIVAR | RAY FLORET COLOR | CAPITULUM FORM AND TYPE |
|---|---|---|
| GALLANT | PURPLE | FLAT DECORATIVE |
| DEEP TELSTAR | LAVENDER | FLAT DECORATIVE |

| CULTIVAR | SPRAY FORMATION | DIAMETER ACROSS FACE OF CAPITULUM |
|---|---|---|
| GALLANT | 13 to 20 cm. PEDUNCLES | 10 to 12 cm. |
| DEEP TELSTAR | 13 to 20 cm. PEDUNCLES | 10 to 12 cm. |

| CULTIVAR | PLANT HEIGHT | FLOWERING RESPONSE PERIOD | LOW TEMPERATURE TOLERANCE |
|---|---|---|---|
| GALLANT | TALL 100 to 110 cm. | 9 WEEKS | 13° C. |
| DEEP TELSTAR | MEDIUM 85 to 95 cm. | 10 WEEKS | 13° C. |

COMPARISONS MADE OF PLANTS GROWN AS SINGLE STEM CUT SPRAY MUMS WITH 14 LONG DAYS IN BOGOTA, COLOMBIA

I claim:

1. A new and distinct plant of *Chrysanthemum morifolium,* Ramat., named Gallant, as described and illustrated, and particularly characterized as to uniqueness by the combined characteristics of flat capitulum form; decorative capitulum type; purple ray floret color; diameter across face of capitulum ranging from 10 to 12 cm. at maturity; uniform nine week flowering response; tall plant height when grown single stem; 13 to 20 cm. peduncles on open, normally terminal sprays; 13° C. minimum temperature tolerance for initiation and development of flowering buds; and very high bud count, with six to nine uniformly developed flowers per stem.

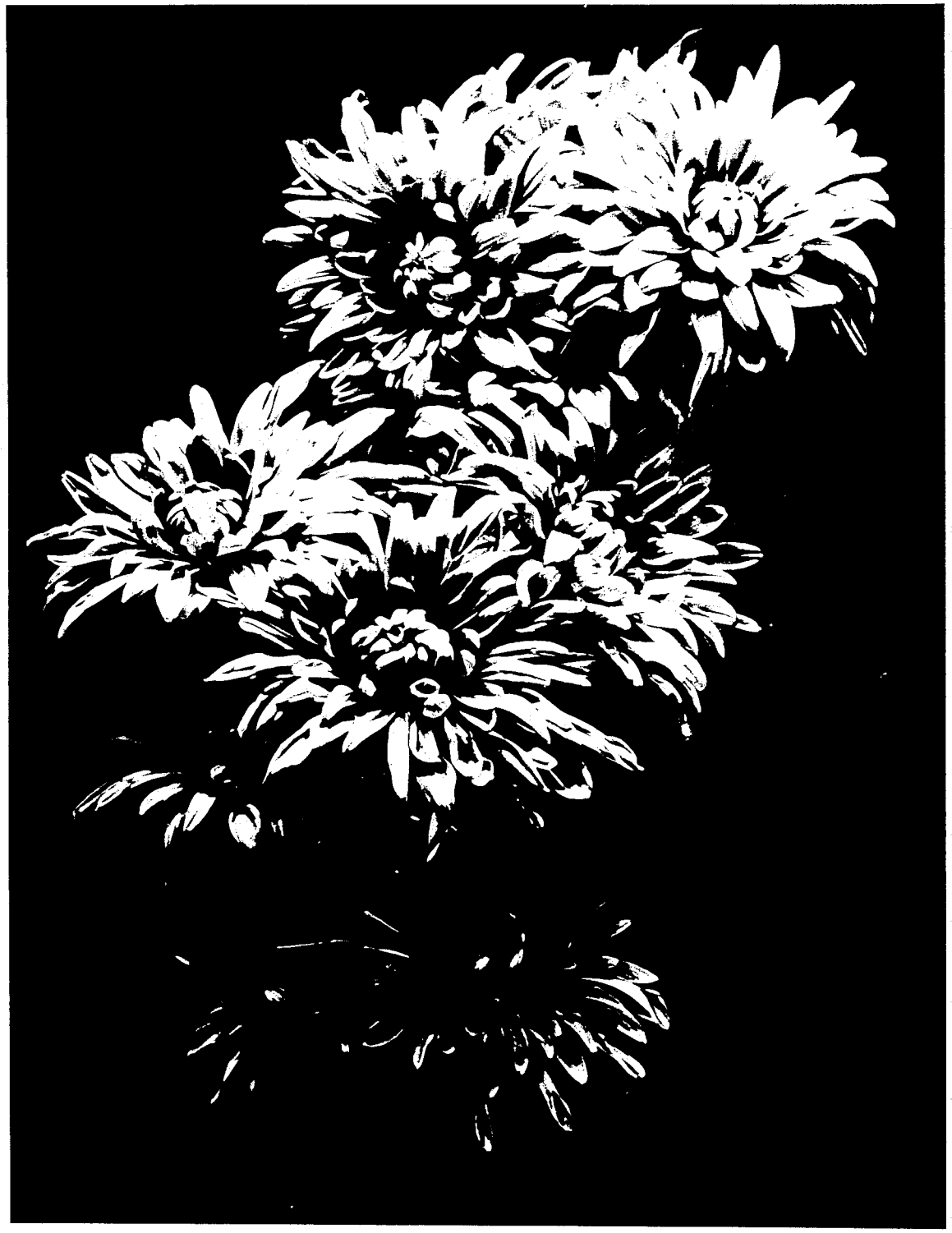

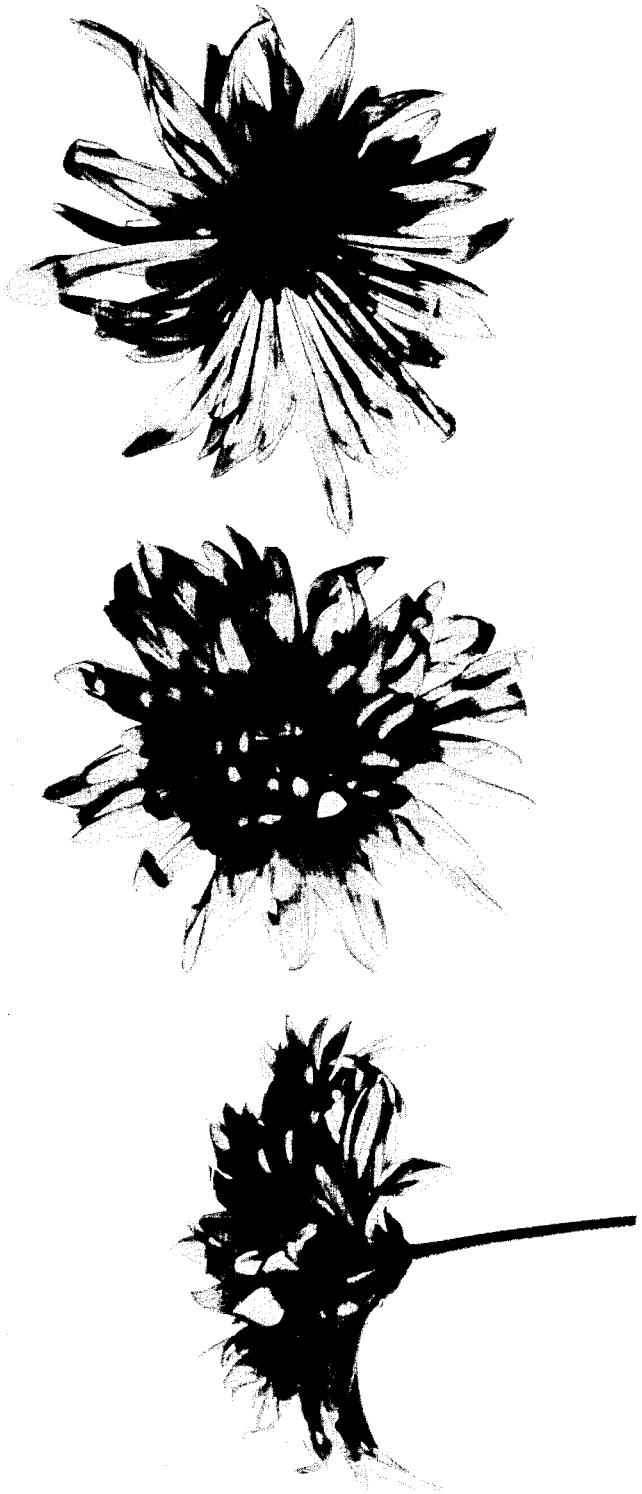

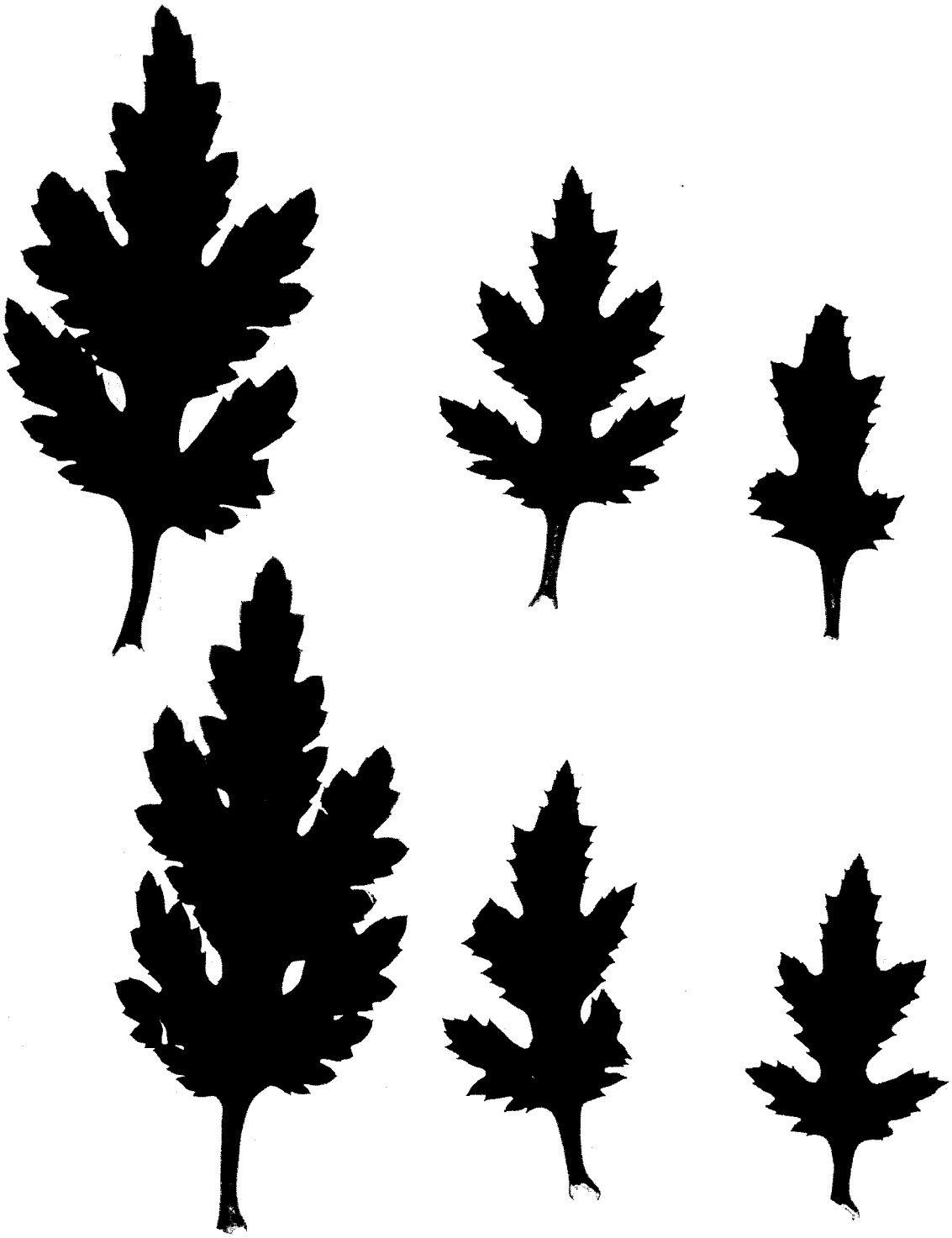

* * * * *